(12) United States Patent
Marchitto et al.

(10) Patent No.: US 10,271,900 B2
(45) Date of Patent: Apr. 30, 2019

(54) INDUCTIVE HEATING OF TISSUES USING ALTERNATING MAGNETIC FIELDS AND USES THEREOF

(75) Inventors: Kevin S. Marchitto, Golden, CO (US); Stephen T. Flock, Arvada, CO (US)

(73) Assignee: ROCKY MOUNTAIN BIOSYSTEMS, INC, Wheat Ridge, CO (US)

( * ) Notice: Subject to any disclaimer, the term of this patent is extended or adjusted under 35 U.S.C. 154(b) by 175 days.

(21) Appl. No.: 12/080,897

(22) Filed: Apr. 7, 2008

(65) Prior Publication Data

US 2008/0249350 A1    Oct. 9, 2008

Related U.S. Application Data

(60) Provisional application No. 60/922,249, filed on Apr. 6, 2007.

(51) Int. Cl.
*A61B 18/18* (2006.01)
*A61B 18/14* (2006.01)
(Continued)

(52) U.S. Cl.
CPC .............. *A61B 18/18* (2013.01); *A61B 18/14* (2013.01); *A61N 2/002* (2013.01); *A61N 2/004* (2013.01);
(Continued)

(58) Field of Classification Search
CPC .......... A61B 18/14; A61B 2018/00452; A61B 2018/0047
(Continued)

(56) References Cited

U.S. PATENT DOCUMENTS 4,889,120 A    12/1989  Gordon
5,057,106 A    10/1991  Kasevich et al.
(Continued)

OTHER PUBLICATIONS

"Electromagnetic radiation." Collins Dictionary of Astronomy. London: Collins, 2006. Credo Reference. Web. May 24, 2012.*
(Continued)

*Primary Examiner* — Michael F Peffley
*Assistant Examiner* — Samantha M Good
(74) *Attorney, Agent, or Firm* — Merchant & Gould P.C.

(57) ABSTRACT

The present invention improves the cosmetic appearance of skin by controllably heating a superficial layer of skin thereby inducing acute tissue contraction or shrinkage and a wound response leading to the production of biomolecules, all of which result in improved cosmesis. The invention incorporates a source of radiofrequency electrical energy coupled to coil, with requisite impedance matching network, thereby resulting in the production of an alternating magnetic field. When tissue is brought into proximity of the alternating magnetic field, inductive heating of the tissue results as a consequence of either or both of dipole formation and oscillation, and eddy current formation. Optionally, cooling is provided to remove heat from the coil, the source of radiofrequency electrical energy, or the surface of the skin alone or in combination. The invention exhibits the significant benefits of, among other things, being non-invasive, not requiring electrical contact with the body of the subject, and providing controllable heating only to a thin layer of tissue.

16 Claims, 10 Drawing Sheets

(51) Int. Cl.
*A61N 2/00* (2006.01)
*A61N 2/02* (2006.01)
*A61B 18/00* (2006.01)

(52) U.S. Cl.
CPC ........ *A61N 2/02* (2013.01); *A61B 2018/0047* (2013.01); *A61B 2018/00452* (2013.01)

(58) Field of Classification Search
USPC ................................ 606/32–33; 607/100–102
See application file for complete search history.

(56) References Cited

U.S. PATENT DOCUMENTS

| | | | |
|---|---|---|---|
| 5,366,443 A | 11/1994 | Eggers et al. | |
| 5,412,182 A | 5/1995 | Chan et al. | 219/635 |
| 5,429,583 A | 7/1995 | Paulus et al. | |
| 5,824,015 A | 10/1998 | Sawyer | |
| 5,897,495 A | 4/1999 | Aida et al. | |
| 6,074,385 A * | 6/2000 | Klopotek | 606/27 |
| 6,148,236 A | 11/2000 | Dann | |
| 6,171,321 B1 | 1/2001 | Gifford et al. | |
| 6,208,903 B1 * | 3/2001 | Richards et al. | 607/101 |
| 6,241,753 B1 * | 6/2001 | Knowlton | 607/99 |
| 6,350,274 B1 | 2/2002 | Li | |
| 6,451,044 B1 | 9/2002 | Naghavi et al. | |
| 6,458,109 B1 | 10/2002 | Henley et al. | |
| 6,656,174 B1 | 12/2003 | Hegde et al. | |
| 6,814,712 B1 | 11/2004 | Edwards et al. | |
| 7,189,230 B2 | 3/2007 | Knowlton | |
| 7,463,251 B2 | 12/2008 | Giraldo | |
| 7,967,839 B2 | 6/2011 | Flock et al. | |
| 2003/0032950 A1 * | 2/2003 | Altshuler et al. | 606/9 |
| 2004/0122494 A1 * | 6/2004 | Eggers et al. | 607/103 |
| 2004/0127895 A1 * | 7/2004 | Flock et al. | 606/41 |
| 2004/0210214 A1 * | 10/2004 | Knowlton | 606/41 |
| 2011/0077451 A1 | 3/2011 | Marchitto et al. | |

OTHER PUBLICATIONS

Anderson, "Fire and ice," Arch Dermatol., 139(6):787-788, Jun. 2003.

Cameron, editor. "Diathermy," Physical Agents in Rehabilitation, 4th Edition, Chapter 10, pp. 202-222, published 2012, originally published 1999.

Cameron, editor. "Pain," Physical Agents in Rehabilitation, 4th Edition, Chapter 4, pp. 46-71, published 2012, originally published 1999.

Cameron, editor. "Physical Agents in Clinical Practice," Physical Agents in Rehabilitation, 4th Edition, Chapter 2, pp. 15-22, published 2012, originally published 1999.

Cameron, editor. "Superficial Cold and Heat," Physical Agents in Rehabilitation, 4th Edition, Chapter 8, pp. 129-172, published 2012, originally published 1999.

Cameron, editor. "The Physiology of Physical Agents," Physical Agents in Rehabilitation, 4th Edition, Chapter 1, pp. 1-14, published 2012, originally published 1999.

Cameron, editor. "Tone Abnormalities," Physical Agents in Rehabilitation, 4th Edition, Chapter 5, pp. 72-105, published 2012, originally published 1999.

Franco et al., "Hyperthermic injury to adipocyte cells by selective heating of subcutaneous fat with a novel radiofrequency device: feasibility studies," Lasers Surg Med., 42(5):361-370, Jul. 2010.

Klein, "Deep Heat," emedicine.medscape.com [online] dated Sep. 25, 2008. Retrieved from the Internet <URL: http://emedicine.medscape.com/article/325046-print>, retrieved on Jan. 27, 2010, 8 pages.

Leitgeb, "Exposure of non-target tissues in medical diathermy," Bioelectromagnetics, 31(1):12-19, Jan. 2010.

* cited by examiner

Untreated

Treated + 2 weeks

Fig 9

Untreated

Treated

INDUCTIVE HEATING OF TISSUES USING ALTERNATING MAGNETIC FIELDS AND USES THEREOF

CROSS-REFERENCE TO RELATED APPLICATION

This non-provisional application claims benefit of priority of provisional application U.S. Ser. No. 60/922,249, filed Apr. 6, 2007, now abandoned.

BACKGROUND OF THE INVENTION

Field of the Invention

The present invention relates generally to the fields of biomedical engineering, biochemistry, medical treatment, and surgical procedures. More specifically, the present invention provides methods, devices, and compositions for inducing changes in tissues, biomolecules, and bioactive molecules. These changes are notably useful for inducing alterations in tissues, most notably in skin, for cosmetic purposes.

Description of the Related Art

Heating of tissue is a fundamental physical event in many different medical procedures. Depending on the time-temperature history of the tissue, a cascade of physical, chemical, and biological events occurs when tissue is heated. These events can lead to a beneficial or deleterious response. One example of a beneficial response is the reduction or elimination of the appearance of skin wrinkles as a result of heat induced tissue contraction.

Skin Wrinkles

Skin wrinkles are often the consequence of advancing age and sun exposure. With increasing age and excessive sun exposure, skin quality deteriorates. This is due, in part, to changes in hydration and epidermal thickness, and on a molecular scale, to a decrease in the amount of collagen in the dermis. Further, subcutaneous fat accumulates or atrophies leading to furrowing of the skin, which produces wrinkles. In today's society, the appearance of skin wrinkles is often viewed negatively and so there is a desire in the community for a means to safely reduce or eliminate wrinkles.

Skin Rejuvenation

For many years, wrinkles have been treated with chemical peels or mechanical dermabrasion, cosmetic medical procedures in which the surface of the epidermis of the skin (the stratum corneum) is removed chemically or by abrasion (sanding), respectively. In the late 1980s, laser ablation procedures for skin resurfacing were developed and approved. Today they remain in use, but are being replaced by laser procedures that are non-ablative and less damaging to surrounding tissues. The goal of these procedures includes tissue contraction, or skin-tightening, as well as induction of a wound response that leads to the generation of new collagen, and hence, dermal thickening. In the mid to late 1990s, another cosmetic technique for skin was developed that involves a non-ablative thermal alteration to skin. This procedure, referred to as radiofrequency (RF) skin rejuvenation, is mediated through capacitive-coupling of radiofrequency energy (e.g. U.S. Pat. No. 7,189,230), using modified electrosurgical devices.

Radiofrequency rejuvenation can result in tissue contraction as tissue structural proteins and proteoglycans thermally denature and coagulate. A second effect of this procedure is a beneficial wound response causing the production of new collagen. More recently, additional devices for skin rejuvenation have been developed that employ ultrasound, high-temperature plasma directed at the tissue, or radiofrequency electromagnetic fields.

All of the current technology can result in deleterious effects in patients and create problems for the operators. For example, laser radiant energy is potentially hazardous to the operator and precautions must be made to safely contain it, and patients often report burns resulting from laser treatments.

Most radiofrequency devices work through capacitive-coupling whereby potentially hazardous electrical current passes through the patient's body, resulting in the creation of radiofrequency electric fields at the interfaces of tissues that are weak- or non-polarity. This effect capacitive coupling can lead to burns at electrodes, and inadvertent heating of collateral tissues, such as adipose tissue. This heating of collateral tissues is an undesirable consequence for skin rejuvenation that can result in atrophy, particularly in fat layers in skin during cosmetic treatments. Further, generation of smoke and charring of tissue is a common consequence of the use of electrosurgical devices. For example, during surgery, an "inadvertent capacitor" can be created between a laparoscope and the electrosurgical probe, resulting in the creation of electrical currents where they are not expected.

The instant invention eliminates the risk of charring and the generation of smoke, as it does not rely on capacitive coupling for its effects. The patient is isolated from the electrical current in the devices and no electrical current is conducted from the applicator or the patient. The invention preferably is used for the direct heating of moist conductive tissues, such as the viable dermis during cosmetic skin treatment, and less efficiently for tissues of low hydration (e.g. stratum corneum), or of low polarity (adipose), thereby providing a safer means for treating skin.

Skin Cooling

When viable tissues reach temperatures of 55 C to 60 C, tissue necrosis may occur. This is one concern during laser and radiofrequency cosmetic skin treatments. Thus, various methods of skin cooling are often employed (Anderson, R R, 2003), including the spraying of cryogen on the skin surface or on an applicator, or applying cold air, water or ice to the skin. One prior art method for the purpose of skin cooling is the application of ice cubes to the skin surface prior to laser treatment, (Gilchrest et al., 1982). These treatments have not proven entirely satisfactory, nor more importantly led to an improved therapeutic response, that is improved blanching of the port wine stain, (nevus flammeus), which is a vascular birthmark consisting of superficial and deep dilated capillaries in the skin that produce a reddish to purplish discoloration of the skin.

Other prior art attempts to provide surface cooling of the epidermis using plastic bags filled with ice placed on the skin surface for five minutes, compressed freon gas used during irradiation, or chilled water spread directly on the area being irradiated have also been explored, (Welch et al., 1983). However, these studies were done with pig cadaver tissue and normally utilized cooling periods of 2 to 14 seconds. The reported results with freon were good in only 28.5 percent of the cases, in some cases, the skin surface was momentarily frozen, and in others, the freon jet was found to overcool the skin surface.

Thus, the prior art is deficient in methods and devices for non-invasive and safer methods of skin rejuvenation induced by high frequency alternating magnetic fields that inductively heat skin tissues. The prior art is also deficient in the use of alternating magnetic fields to inductively heat conductive dermal tissues with a high degree of specificity. The prior art is also deficient in methods and devices to target during the skin rejuvenation process only conductive dermal tissue and have little effect on fat and skin surface tissues. The present invention fulfills this longstanding need and desire in the art.

SUMMARY OF THE INVENTION

The present invention is directed to a method of treatment of tissues in a subject, most notably for cosmetic treatment of skin. The method involves creating a high-frequency alternating magnetic field that, when directed in proximity with tissue, results in the production of heat through inductive coupling with the tissue thus resulting in the desired biologic effect. Representative examples of such biologic effects include, but are not limited to coagulation, cauterization, tissue contraction or shrinkage, and induction of a wound response that leads to biomolecular changes such as the production of collagen by cells.

The present invention also is directed to methods to coagulate tissue. The coagulation process may be beneficial in ablating tissue, fusing tissue, and in improving skin cosmesis.

The present invention is directed further still to a method of monitoring the treatment process in tissue. The heating process may be controlled by feedback monitoring and adjustment of the heating process in accord to the results. Methods of monitoring include, but are not limited to, detection heat generation, monitoring eddy current formation in the tissue, ultrasound detection of tissue alterations or changes in impedence in tissues that lead to an impedance mis-match between the magnetic field applicator and the radiofrequency generator.

The present invention is yet directed further still to a method of cooling the surface of the skin during a treatment with. The cooling method of the present invention preferably involves cooling of a thermally conductive surface in contact with the skin. This may be accomplished by circulating coolant through the component in contact with the surface of the skin, or the contact component may be cooled by circulating coolant through the device coil component, or by directing cryogenic liquid or gas on the surface of the skin, to the contact surface, or the device coil component, before, during or after treatment.

The present invention is directed further still to a method of inducing a beneficial wound response in tissue by exposing the tissue to a high-frequency alternating magnetic field that induces the movement of charged species within the tissue leading to various biologic responses, some of which are induced by the concomitant production of heat in the tissue. One beneficial would response is the production of new collagen in the skin and dermal thickening.

The present invention is yet directed further still to a device for altering tissue incorporating a source of electromagnetic energy, a cooling system, an induction coil, an impedence matching network, and optionally, a means of controlling the process.

The present invention is directed further to a device for treating tissue incorporating a hand piece coupled to the energy output of a radiofrequency generator, whereby the hand piece incorporates an impedance matching network, a cooling system, and optionally a feedback mechanism to ensure proper treatment of the tissue. Optionally, a mechanical or pneumatic tissue-shaper, which can manipulate the tissue into a beneficial position and shape proximal to the hand piece is incorporated.

The present invention is yet directed further still to a device for altering tissue incorporating a source of electromagnetic energy, an induction coil, a cooling system, an impedance matching network, and a means of controlling the process through feedback monitoring by detection of eddy currents, or detection of an additional source of radiant energy, plasma energy, acoustic energy, bipolar electrosurgical energy, or monopolar electrosurgical energy.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

One embodiment of the present invention provides a method of treatment for one or more tissue in an individual, comprising positioning an alternating magnetic field in proximity of the tissue, inducing heat therein, and thereby effecting treatment.

Radiofrequency Power Supply

The invention consists of a source of radiofrequency (RF) electrical energy, normally a radiofrequency generator such as sold by Comdel, Inc. (e.g. CV1000 or CV500, 40.68 MHz; Gloucester, Mass.). The electrical output of the generator is coupled to an applicator consisting of an inductor in the form of a coil (for the generation of a magnetic field), which is further part of an impedance matching network that may additionally comprise a capacitor. In some cases applicator may include an antenna (for the production of an electrical field). The source of energy used may be a constant current or a constant voltage power supply or may be a modulated current or a modulated voltage power supply. The power-supply is able to produce radiofrequency energy with a power in the range 10-10,000 W and, depending on the application, may be more preferably in the range of about 100 to about 1000 W. The power-supply may typically operate at frequencies of 100 kHz to 2.4 GHz. Preferably the frequency range is about 100 kHz to about 5.8 GHz and, more preferably, the frequency range is at or near, or between 415 kHz to 4 MHz, 13.56 MHz, 27.12 MHz, 40.68, 67.8 MHz, 95 MHz, 433.92, 915 MHz, 2.4 GHz. The power-supply may optionally be one used in electrosurgery. Beneficially, the radiofrequency generator should be frequency-agile; that is, as the impedance of the load changes somewhat, the frequency output of the radiofrequency generator changes slightly to provide a better impedance match between the load and generator and so to maintain the output power within a controllable tolerance.

Applicator

Figure 1:
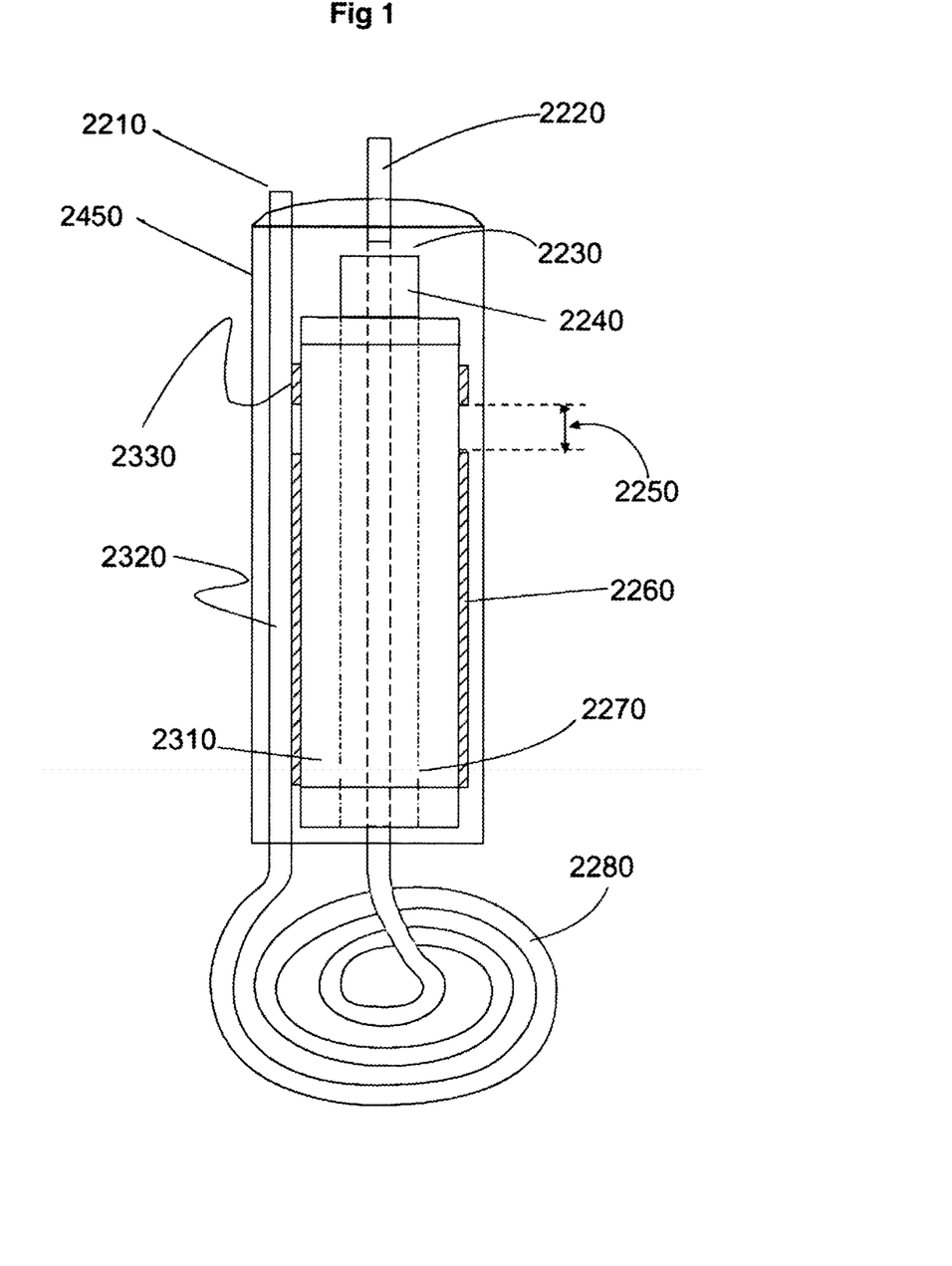
FIG. 1 depicts an applicator that transduces radiofrequency electrical energy into a magnetic field.

FIG. 1 is a sectional view of an applicator used to produce a magnetic field. A center copper tube 2220, which serves to conduct the radiofrequency electricity but also as an input for refrigerant, is surrounded by a TEFLON® cylinder 2240. Endcaps 2230 and 2270 serve to position and hold the copper tube within the TEFLON® cylinder. The center copper tube 2220 is formed at the distal end of the applicator into a coil, 2280, which then is fixed parallel 2320 with the center copper tube and directed to an exit 2210 out of the applicator; the coolant is directed out through exit 2210. In order to provide impedance matching between the radiofrequency generator and applicator, a ceramic insulator 2310 is positioned around the TEFLON® cylinder 2240. The ceramic insulator has two capacitor rings, 2330 and 2260, made up of copper pipe. The pipe 2320 is in electrical contact with the capacitor rings. By adjusting the spacing 2250 between the two capacitor rings, the impedance match between the radiofrequency generator and applicator can be effected. The applicator is encased in a copper cylinder 2450 attached to the ground shield of the coaxial wire in order to shield any stray radiated radiofrequency.

HandPiece

Figure 2:
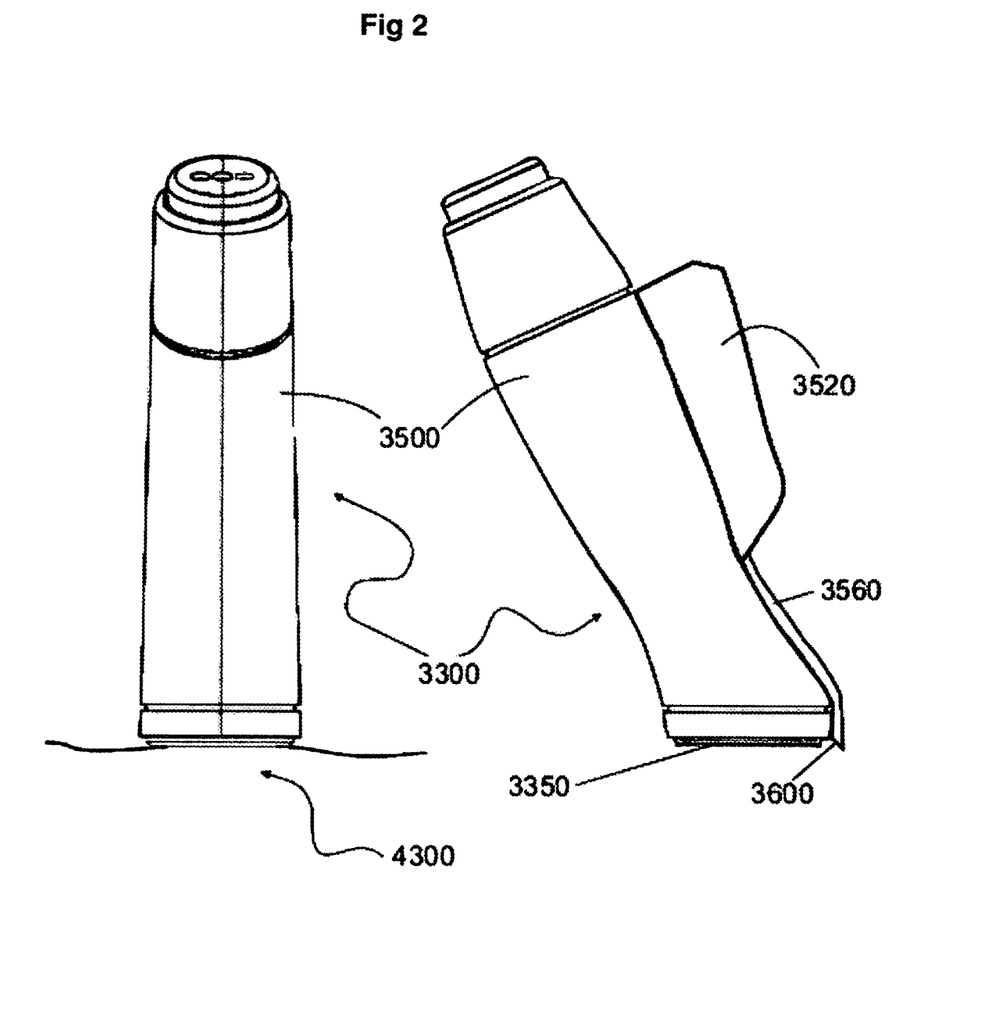
FIG. 2 depicts a hand piece incorporating a magnetic field applicator with optional cooling system.

FIG. 2 shows a view of one design for a hand piece 3300, which is made of an electrically non-conductive material such as plastic, which surrounds the applicator. The main housing 3500 is optionally attached to a disposable shield 3350, which serves to maintain cleanliness of the part of the handpiece which comes into contact with the skin 4300. Optionally, the handpiece incorporates a coolant (for example, R-134a) contained in a housing 3520 and directed through a solenoid and pipe 3560 to an exit nozzle 3600. This coolant can be controllable directed to the treated tissue before, during and/or after the treatment in order to limit the heating of the very superficial skin.

Cooling Endplate

Figure 3:
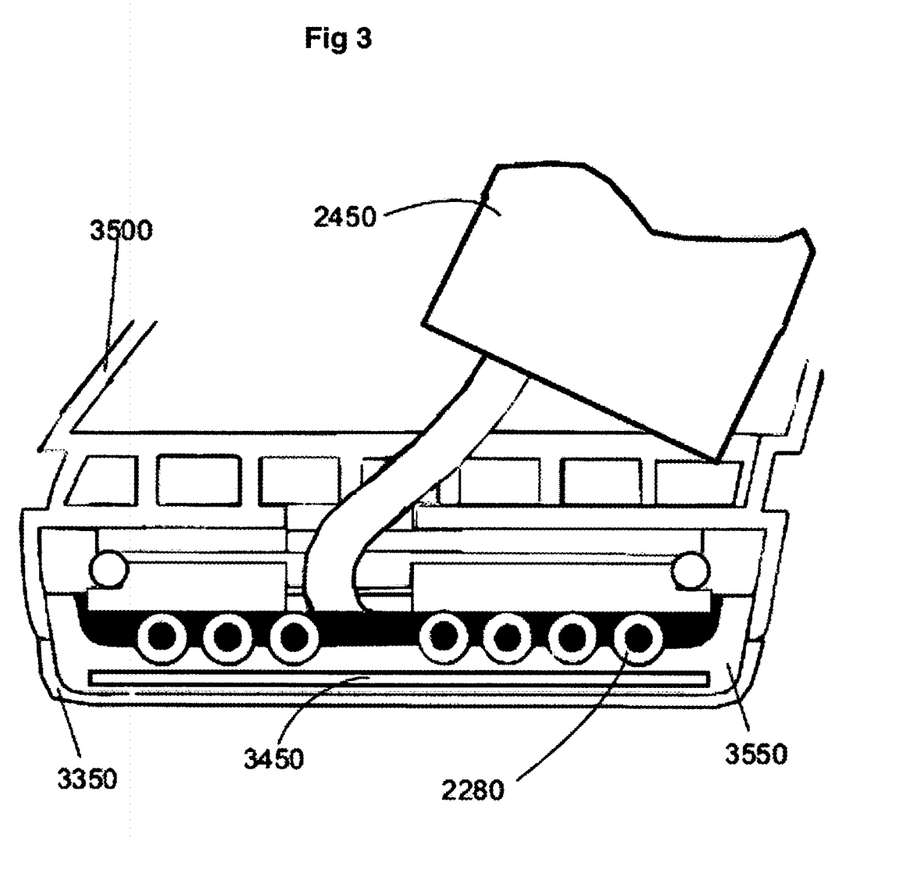
FIG. 3 depicts the endplate of the hand piece.

FIG. 3 shows a view of an endplate 3550 on the distal end of the hand piece housing 3500. The endplate is in intimate thermal contact with the coil 2280, which has circulating refrigerant within, and so the endplate is cooled. This coolant may optionally be supplied from a circulating chiller utilizing water and antifreeze. Alternatively, gas such as air, nitrogen, freon, R-12, R-134a, and carbon dioxide could serve the purpose of cooling. Keeping in mind that the disposable shield 3350 is very thin and/or is highly thermally conductive, it serves to cool the skin before, during and/or after the treatment in order to limit the heating of the very superficial skin and increase comfort for the subject. FIG. 3 also shows an optional Faraday shield 3450, which is a conductive element intended to reduce capacitive coupling of coil to the subject, and so to minimize any stray electric field. Note that the cooling endplate may be in intimate contact with the coil in order to provide optimal thermal conduction. This may be accomplished by molding or by forming the plate around the coil. As shown in FIG. 2, cooling of the skin may be realized by spraying the skin with a coolant before, during or after treatment.

Pneumatic Applicator

Figure 4:
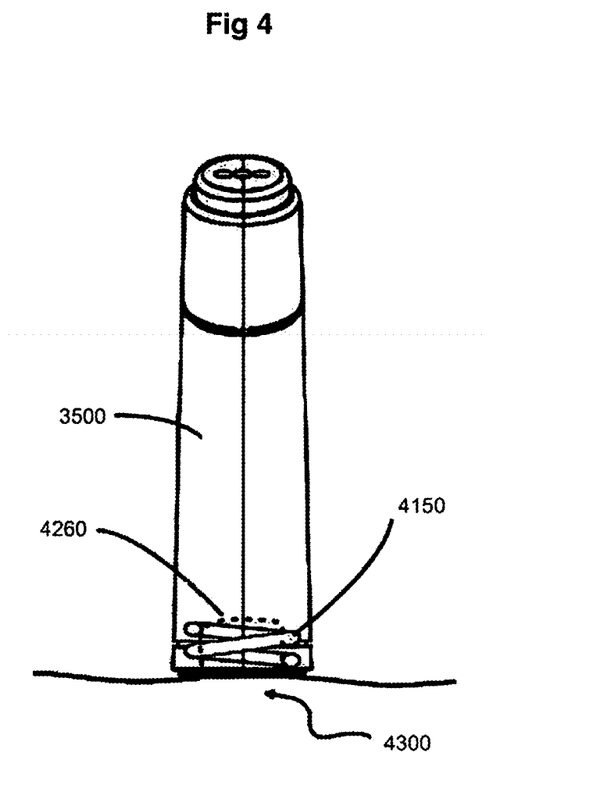
FIG. 4 depicts a hand piece incorporating a solenoid-type inductor and positioning of tissue using pneumatic pressure.

FIG. 4 shows a partial view of an applicator incorporating a two-turn solenoid coil 4150, the bore of which surround tissue 4260 which extrudes from the skin 4300 up into the bore as a result of negative pneumatic pressure within the housing 3500. As the magnetic field within the turns of a solenoid is very much stronger than the field outside of a pancake coil, and the geometry of the tissue within the bore is different than illustrated in FIG. 2, the power required to obtain an effect is reduced and the effect on tissue can be more beneficial.

Combined Devices

In some aspects of this embodiment, the treatment may be inductive, or conductively or radiatively applied in combination with the use of an alternating magnetic field. Additionally, the energy may be pulsed in order to improve the thermal kinetics of the tissue heating. Examples of applied energy are radiofrequency energy, radiant energy, or vibrational energy. The radiofrequency energy may have a frequency from about 20 kHz to about 40 GHz, and may be applied using coils, electrodes or one or more antennae. The radiant energy may have a wavelength from about 600 nm to 11 m. The vibrational energy may be sonic or ultrasonic with a frequency from about 20 Hz to 80 MHz. In the case of inductive heating, the energy may not be incident on the target, but may be induced in the target to be converted from one form to another.

In certain aspects, combined devices, using induction plus an energy source (e.g. laser or ultrasound) may enhance the effects or be used to combine certain treatments. Because the interaction of laser energy and ultrasound waves with tissue is physically different than the present invention, it is anticipated that a different effect can be elicited. An applicator of radiant energy may consist of an optical assembly, which focuses the radiant energy on the relevant target or below the target surface, to get a sub-surface effect sparing the superior surface. A pressure-wave applicator may consist of a focused ultrasound transducer, which is coupled to the target tissue with an acoustic impedance matching material, such as gelatin, mineral oil or glycerin.

Feedback Monitoring and Safety Interlocks

In its preferred embodiment (FIG. 1), where a magnetic field is produced, the heating effect in tissue tends to change the electrical properties of the tissue. As the tissue alters the electrical impedance that the radiofrequency generator sees, it is possible to use this change to monitor the heating process. For example, as the impedance of the skin changes, the impedance mismatch between the radiofrequency generator and the tissue/applicator increases and so the power reflected back into the radiofrequency generator increases. It is this increase in power that can be used as a signal to eventually halt the application of energy. Alternatively, the change in tissue can be detected using ultrasound or by detecting changes in eddy current formation.

As the tissue treatment process is initiated, the applicator (FIG. 1) and most notably the coil 2280, endplate (FIG. 3, 3550), and tissue heat up; when the radiofrequency energy ceases, they cool down. Such temperature changes can easily be monitored by devices such as thermocouples or thermistors. As such devices can behave erratically in the presence of strong electromagnetic fields, devices such as infrared thermometers may be more suitable to monitor the temperatures.

Transducers monitoring the temperature and power output of the radiofrequency generator, the reflected power into the generator, the presence of water flow into the applicator (and generator, if it is required), and the presence of a short-circuit anywhere (indicted by a rapid rise in current in the generator and/or applicator, are an important safety feature in the present invention. Other optional safety interlocks include mechanical or electrical transducers between the disposable shield (FIG. 3, 3350) and the housing of the hand piece; if a shield is not present, the RF generator would not engage. Encoding of the interlock in the shield would ensure that a particular shield is only used on a particular patient. Thermal switches are incorporated within the device to shut it down if overheating occurs. Fast breakers quickly cut off the output if a power-output transient occurs. Multiple interlocks are incorporated within the device, which prevents running the device with the cover removed. A foot pedal optionally is incorporated in order to minimize the possibility of unintentional activation of the device.

The induced magnetic field may also be actuated upon detection of a load. A relatively small current may be applied to the device while the device is not in proximity to a tissue target. As the device becomes proximal to the target, the change in impedance is detectable, and this may be used as a signal to increase power to the device. This safety feature minimizes the exposure of the handpiece components to significant power load when the device is not applied to tissue, thus potentially reducing wear of the device.

Methods of Treatment

The device may be used to induce changes in tissue by applying alternating magnetic fields to the tissue such that currents are induced within the tissue (eddy currents). These currents encounter resistance and the result is the generation of heat. These eddy currents form most efficiently where there is a moist, polar environment, thus enabling electron displacement or ion flow within the target. Thus, for example, in skin, the generation of eddy currents in the moist underlying dermis is favored over the superficial dehydrated epidermis and stratum corneum layers, and the underlying, more non-polar adipose layer. This results in preferable heating of conductive tissues over non- or weakly-conductive tissues.

Variations in cooling of the skin surface may be achieved by increasing the volume of coolant to the device, or surface of the skin. These variations may be optimized to provide additional protection of the tissue proximal to the device from the effects of heating.

A scaffold or lattice structure may be placed within tissues to provide support. The structure may be fixed or fused in place using methods described herein. For example, localizing a scaffold made of polylactic acid, or a similar polymer in proximity to fat layers found in or under skin could prove beneficial in the treatment of cellulite fat. Cellulite produces an unattractive profile on the surface of skin due to the fat being squeezed between tissue structures resulting in upwelling of "fingers" of fat, which then distend the skin surface. Cellulite's cause is unclear, although it may result from fatty distension of the superficial fascia, which connects the dermis to the deep fascia. Attachment points to the dermis may be patent while surrounding areas lose structure and bulge, producing the "cobblestone" appearance on the surface of the skin. By increasing the number of attachment points, or by fixing a mesh-like substrate in place to minimize bulge, or by heating the fat to achieve melting and flowing into the scaffold, cosmesis may conceivably be improved. The devices and methods described herein may be used to heat and melt fat layers.

Another embodiment of the present invention allows for treatment of acne, hair removal or treatment of varicose veins. It has been determined that the production of a critical amount of heat in tissue can lead to a cascade of events that results in a therapeutic effect. Acne can be treated by causing thermal damage in the affected skin, and hair removal can result from thermal damage to the hair follicles. The exact biologic mechanism behind these treatments is unclear, but tissue tightening may play a role. Alternatively, sublethal damage to the hair follicles can actually result in stimulating hair growth. Sublethal damage leads to a cascade of wound-response events such as the production of cytokines, interleukins and heat-shock proteins. These endogenous events can be beneficial and probably underly the salient events in, for example, stimulating hair-growth. In any case, the instant invention can induce all of these events.

Treatment of skin wrinkles can sometimes employ botulism toxin, whereupon an injection of toxin in or around the nerves associated with the wrinkle temporarily relax the muscle leading to reduction in the appearance of the wrinkle. Recently, electrosurgical ablation of the nerve has been shown to result in a good cosmetic effect and may benefit from being permanent. The problem with electrosurgical ablation of the nerves are the same as the problems associated with electrosurgical generators in other procedures. The present invention provides a means with which to ablate the nerve in a non-contact mode.

Coagulation is a very important technique in surgery as it provides a means to kill tissue without dissection, thus eliminating potentially toxic smoke and char, and by not removing tissue, allowing for mechanical integrity to be maintained for a period of time. Standard electrosurgical and electrocautery devices usually produce smoke when used to coagulate tissue (smoke is a potential source of carcinogens or viruses), and dry tissue tends to stick to the electrosurgical electrode which then results in re-bleeding when the electrode is removed from the treatment site. A non-contact way of coagulating tissue, using the instant invention, would be or paramount importance in surgery. The instant invention exhibits the benefit and when the tissue is heated and dessicates, coupling between the magnetic field and tissue decreases thus limiting the heating and eliminating the possibility of smoke or charring.

As described below, the invention provides a number of therapeutic advantages and uses, but such advantages and uses are not limited by such description. Embodiments of the present invention are better illustrated with reference to the FIGS. 1-10, however, such reference is not meant to limit the present invention in any fashion. The embodiments and variations described in detail herein are to be interpreted by the appended claims and equivalents thereof.

The following examples are given for the purpose of illustrating various embodiments of the invention and are not meant to limit the present invention in any fashion.

EXAMPLE 1

Applicator

Figure 5:
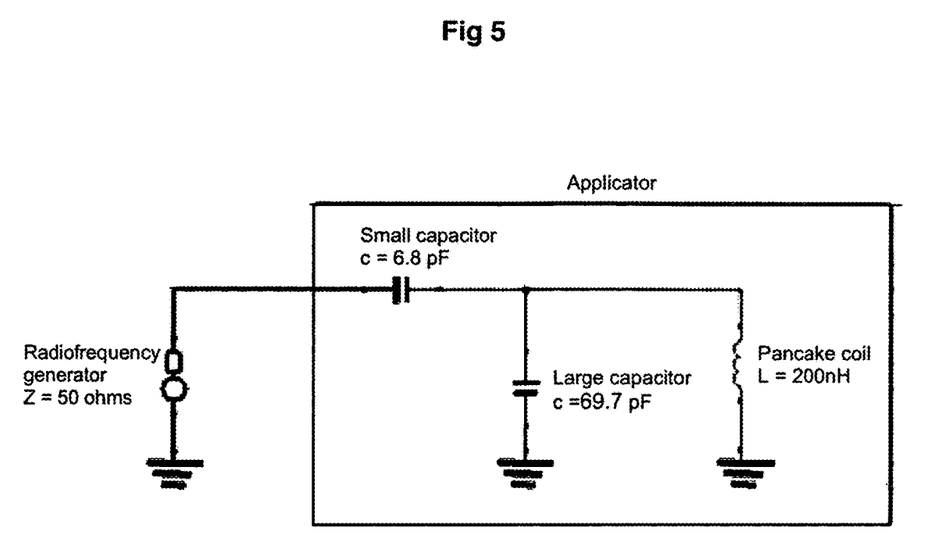
FIG. 5 depicts a circuit diagram of the applicator.

The pancake coil is made from 3.5 turns of 0.125" OD copper refrigeration tubing and has a diameter of 1.4". The coil must be hollow tubing to allow water or other cooling fluid to flow through it and dissipate the ~500 W of heat generated. The main capacitor (FIG. 1, 2260) has a value of ~70 pF which resonates with the coil at 40.68 MHz (FIG. 5). Earlier prototypes were made with a TEFLON® dielectric (er=2.2), but the size of the capacitor became too unwieldy to use in a handheld device. Capacitance can be calculated using the formula for a cylindrical capacitor: $C=(2*p*er*ev)/(ln(b/a))$, where, C.=capacitance in pF per unit length, er=dielectric constant (9.8), ev=permittivity of free space=8.85e−12 f/m, b=outer diameter, a=inner diameter The length of the capacitor is inversely proportional to the er of the dielectric used, so alumina was chosen for its high er and its other desirable properties: Good thermal conductivity—30 W/m*K; High dielectric strength—220 ACV/mil; High dielectric constant—9.8; Available in tube form at low cost; Dimensions compatible with available copper pipe sizes. The particular alumina tube used is 3.5" long, 0.625" OD, 0.500" ID, 99.8% alumina (CoorsTek part #65677). The inner and outer "plates" of the cylindrical capacitor are copper pipes that fit closely to the inner and outer diameters of the alumina tube.

It is critical that the copper tubes fit the alumina as closely as possible, as any air gaps will act as low value series capacitors and offset the advantage of the high er material. Since it is impossible to completely eliminate the air gaps, the entire capacitor assembly is potted in silicone with a er of 2.7 to regain some of the capacitance lost by the gaps, and also to help prevent the high voltage RF arcs which are bound to occur at these high voltages. The silicone, through vacuum encapsulation, completely surrounds all high voltage points on the device. The tuning capacitor (FIG. 1, 2330), is formed in the same way as the main capacitor, although much smaller in value and size.

Shielding was found to be an important part of the design to reduce circuit detuning caused by the operator's hand, as well as reduce stray radiation from the connecting coax and radiofrequency generator. The shield encloses all the internal workings of the device, and is made from 1" copper pipe and an end cap. The shield also serves as a liquid tight container to hold the silicone (MOMENTIVE RTV615) during the vacuum encapsulation process.

Water-cooling is used to effectively cool both the coil and the coaxial capacitor assembly. Water flows in series through the center capacitor pipe, then the coil, and back through the copper tubing soldered to the outer capacitor pipe. At a power level of 500 W and 0.75 liters/min flow, the water temperature rise is about 9° C.

A resonant circuit was the topology chosen to maximize the current in the coil because this type of circuit has the property that the circulating current is approximately Q times the applied current, and the Q of this circuit is about 60. The primary goals of the circuit are to maximize the current in the coil as well as provide a good impedance match to the 50 ohm RF generator driving it.

The alumina tube is cut to length using a wet cutting diamond saw. The inner pipe is then prepared by turning it down on a lathe to a size that just slides into the ceramic without forcing it. Copper disks and short lengths of 0.125" copper tubing are soldered into the ends of the pipe, one going to the flexible silicone water tubing, and the other to the pancake coil.

A small batch of RTV615 is mixed up and de-aired in a vacuum chamber using a Welch 1400 vacuum pump. The mixture is considered de-aired after it foams up and then recedes (~30 minutes). About 1 ml of the RTV615 is poured into one end of the vertically held inner pipe/ceramic assembly and cured at 100 deg C. for one hour, forming a silicone "plug" in that end to prevent the liquid RTV615 from running out during the next step. After cooling, the assembly is inverted and more RTV615 is poured into the other end and allowed to sink in and fill the gaps between the inner pipe and ceramic under vacuum. After sufficient time in the vacuum (no more rising air bubbles visible), the assembly is removed from the vacuum and again cured at 100 deg C. for one hour.

Adhesive backed copper foil tape is tightly wrapped on the outer diameter of the ceramic assembly over a distance slightly shorter than the outer capacitor pipe. The purpose of the tape is to get a tight fitting conductor around the ceramic with minimal air gaps. The tape is mechanically weak and not thick enough to adequately conduct the heat generated, so copper pipe couplers are then bored out to slide over the layer of copper tape, and will be soldered in place once the initial tuning is completed. The "ring" pipe is bored out to tightly fit the ceramic at this time as well. About 0.4" of free ceramic is left on the end for high voltage insulation and spacing.

Next, the pancake coil is wound from the 0.125" refrigeration tubing, and the short end of the tubing from the center is coupled and soldered to the tubing stub on the capacitor assembly. The other (long/grounded) end of the tubing is positioned parallel and against the outer pipe (ground), and is temporarily held in place with copper tape for tuning.

A length of test coaxial cable from a network analyzer is temporarily soldered between ground and the ring. The outer pipe and ring are slid back and forth to obtain an impedance match at a frequency higher than the final operating frequency, knowing that the frequency will drop after encapsulation with silicone. Once the correct position is found, the grounded tubing of the pancake coil is soldered along the outer pipe and the gap between the copper foil and outer pipe is flooded with solder.

The silicone water tubing is now attached to the other stub of 0.125" tube on the inner pipe with a bus wire "hose clamp" and the connection covered with heatshrink. The TEFLON® sleeve is then slipped over this connection for high voltage insulation.

At this point the 1" copper shield pipe is positioned over the inner workings, with the grounded end of the coil's copper tubing exiting the shield through a slot in the side. The flexible silicone water hose and coaxial cable are fed through holes in the pipe cap; the coaxial braid is soldered to the inner wall of the shield, and the coax center conductor to the ring on the ceramic assembly. After pressing the pipe cap in place, and centering the ceramic assembly in the shield, the ground tubing is soldered to the shield and the slot filled with solder for a liquid tight seal. A final tuning check is made with a network analyzer with the shield in position, and any necessary pre-encapsulation adjustments are made.

Next, another (~80 g) batch of RTV615 is prepared and de-aired in the vacuum chamber as before. With the device held vertically and open at the top, the assembly is slowly filled with RTV615 and then vacuum pumped for about an hour to remove all air bubbles. The vacuum process is complete when air bubbles stop rising to the surface. The device is then removed from the vacuum and cured for 4 hours at 65° C. The longer, lower temperature curing cycle is used because it is below the coaxial cable's maximum temperature rating. After curing and cooling, the second silicone water hose is attached to the copper ground tubing with a bus wire "hose clamp" and the connection covered with heat shrink.

EXAMPLE 2

Tissue Tightening In Vitro

Ovine and human tissue samples were cut into 2 cm×2 cm sections and inductively treated using 400 W power generated from a an ENI 6B power supply operating at 13.6 MHz. The coil was 2 cm in diameter and placed 2 mm from the tissue. Exposure was for 20-30 seconds. Samples of lung, artery, and skin demonstrated macroscopic shrinkage of approximately 5-20% depending on length of exposure. Skin and lung samples were placed in formalin and evaluated by thin section histology. Examination of Masontrichome stained sections demonstrated that collagen fibrils were packed more closely together in the treated versus untreated sections.

Figure 6:
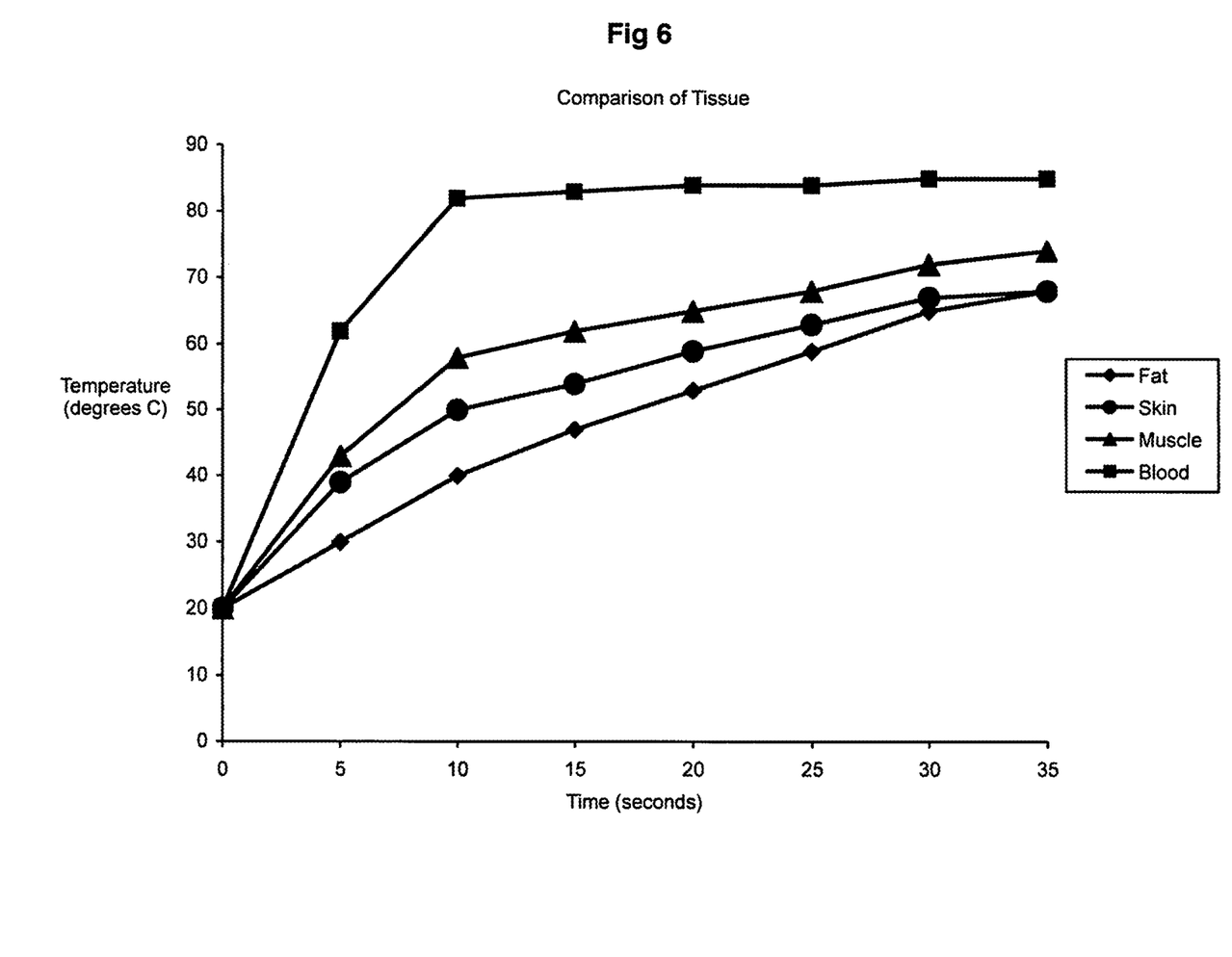
FIG. 6 shows measurements taken at 27 MHz and 600 W. Bovine muscle, bovine fat, ovine skin, and human blood were used for comparison. The tissues were cut to 2.times.2.times.5 cm samples. Each sample was placed directly on the cap of the 27 MHz device and imaged from above with a Raytek IR thermometer. The device was activated and the time to heat was recorded. (n=3 for each tissue type).

FIG. 6 shows measurements taken at 27 MHz and 600 W. Bovine muscle, bovine fat, ovine skin, and human blood were used for comparison. The tissues were cut to 2×2×5 cm samples. Each sample was placed directly on the cap of the 27 MHz device and imaged from above with a Raytek IR thermometer. The device was activated and the time to heat was recorded, (n=3 for each tissue type).

Figure 7:
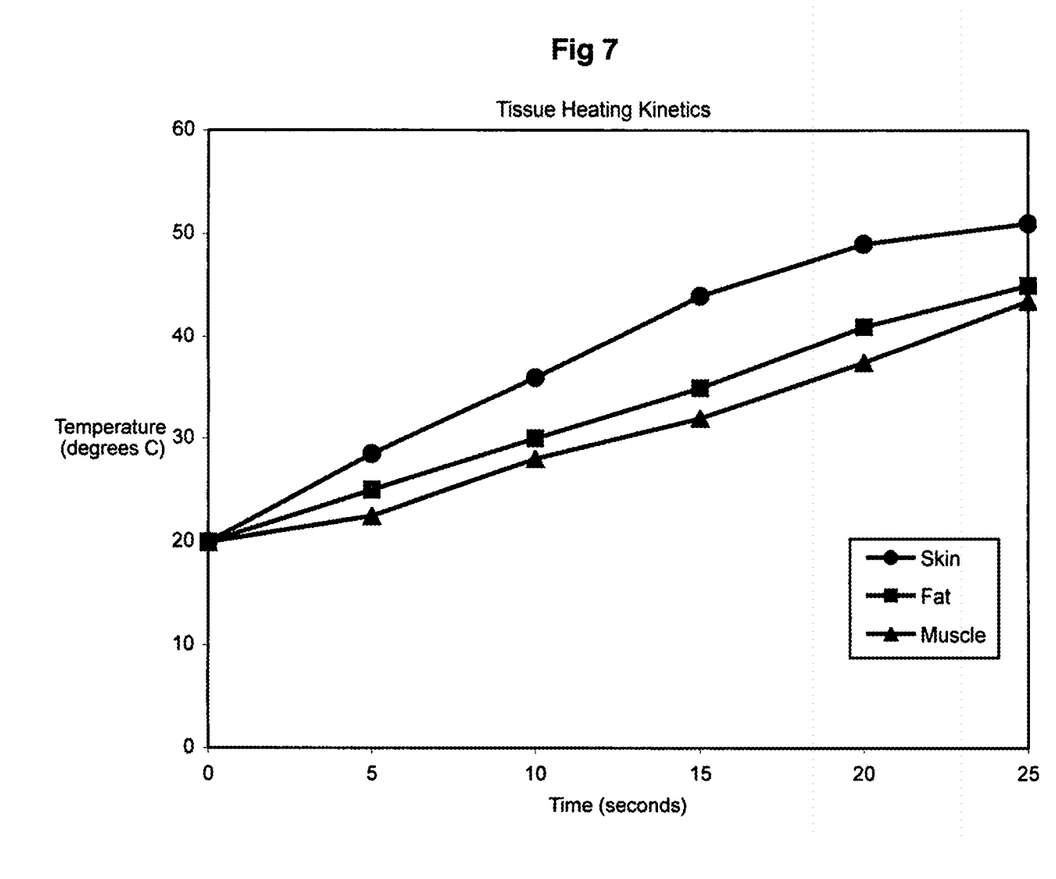
FIG. 7 shows porcine fat, muscle and skin were used for comparison. The tissue samples were measured for thickness to ensure consistency between samples. The samples were between 1.5-2.0 mm in thickness. The samples were placed on the faceplate which is 4 mm thick PVC and imaged from above with a Raytek IR thermometer. The device was turned on and the time for the sample to reach 70.degree. C. was recorded. The IR thermometer is limited to recording the tissue surface opposite that which is in contact with the device. Therefore, it is believe that the actual temperature of the tissue was greater than indicated on the graph.
Figure 8:
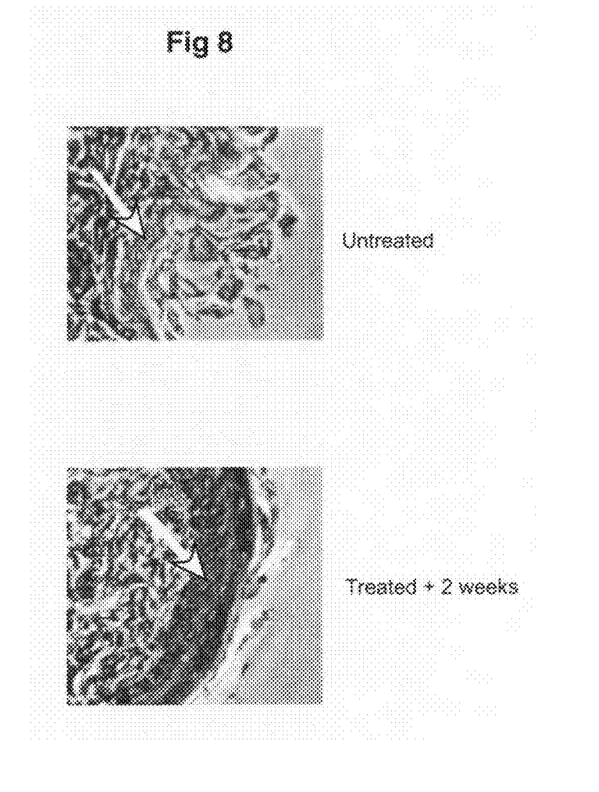
FIG. 8 shows biopsied samples at each time point demonstrating a thickening of the dermis as compared to untreated controls.

FIG. 7 shows porcine fat, muscle and skin were used for comparison. The tissue samples were measured for thickness to ensure consistency between samples. The samples were between 1.5-2.0 mm in thickness. The samples were placed on the faceplate which is 4 mm thick PVC and imaged from above with a Raytek IR thermometer. The device was turned on and the time for the sample to reach 70° C. was recorded. The IR thermometer is limited to recording the tissue surface opposite that which is in contact with the device. Therefore, it is believe that the actual temperature of the tissue was greater than indicated on the graph.

EXAMPLE 3

Tissue Tightening and Dermal Thickening In Vivo

Rat skin was treated with the magnetic field coil device at 40 MHz and 350 W power delivery. The device was held juxtaposed to the skin of anesthetized rats until visible shrinkage was evident without cooling (treatment time tt=24 seconds), with cooling (that is, with the refrigerant circulating through the coil and endplate, tt=29 seconds) and at tt=27 seconds. A grid was drawn on the back of the animal prior to treatment and was photographed before and after treatment and post-treatment day one. The image was digitized and the grids were compared down to the pixel for acute shrinkage. The treatment site was biopsied on post-treatment day two for acute wound response and on post-treatment day 21 to ascertain collagen deposition. Temperature of the epidermis was also measured following treatment. After treatment, the temperature of the surface of the skin was at or around 42° C. By measuring the distance between the gridlines on the skin, it was possible to determine that acute shrinkage of 5% with cooling and 8.5% without cooling occurred. After 1 day, the skin exhibited a sustained shrinkage of 2.5% with cooling and an increase to 15.9% without cooling. Consistent results were obtained with guinea pig skin, which is known to better mimic human dermal tissue. Treated guinea pig skin shrunk 10.9% with cooling and 11.6% without cooling immediately following treatment.

EXAMPLE 4

Tissue Tightening and Dermal Thickening Using 27.2 MHz

Figure 9:
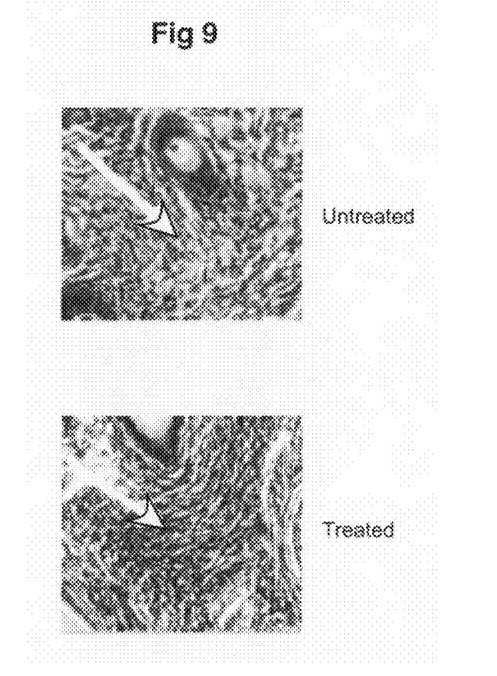
FIG. 9 shows biopsied samples at each time point demonstrating a production of neo-collagen in treated tissues as compared to the untreated controls.
Figure 10:
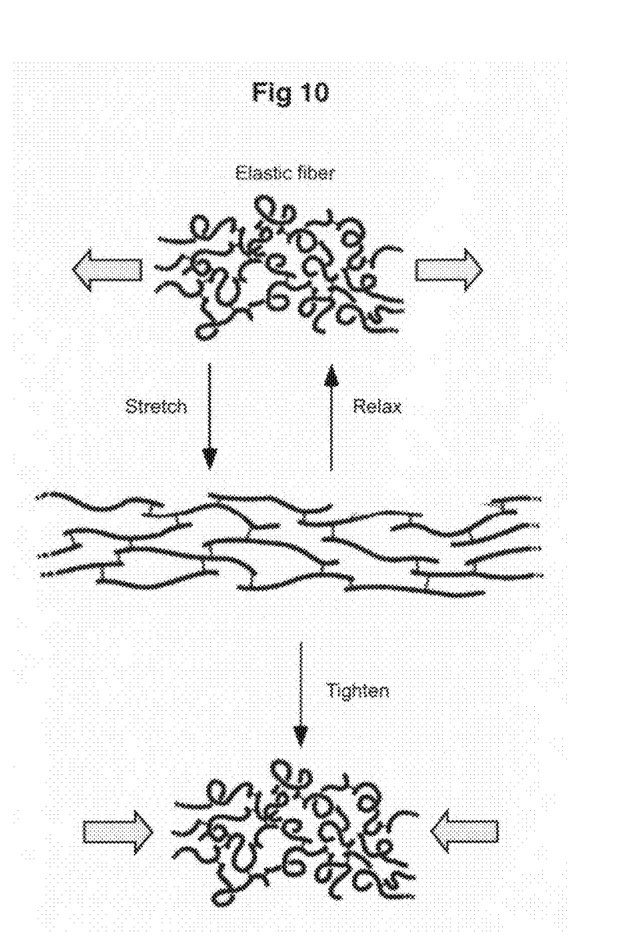
FIG. 10 shows a model of the expected mode of action produced by inductive heating on collagen within the treated tissues.

The dorsa of four Sprague-Dawley rats were shaved, then the skin was inductively treated using 600 W power generated from a 27.2 MHz power supply. The two-turn pancake coil was 1.5 cm in diameter, and placed against the tissue using a 2 mm spacer composed of TEFLON®. Exposure was from 5 to 10 seconds and cooling of the coil was used. Contraction of the tissue was noted after several seconds of treatment. Biopsies were taken at 21 or 28 days, and histologically stained using eosin or Mason Trichome. Biopised samples at each time point showed a thickening of the dermis as compared to untreated controls, (FIG. 8) as well as production of neo-collagen (FIG. 9). FIG. 10 shows a model of the expected mode of action produced by this inductive heating using alternating magnetic field energy on the collagen within the treated tissues.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

REFERENCES

Anderson, R R, Arch Dermatol, 2003, 139:787-788.
Bass, et al, Laser Surg. Med. 1995: 17:315-349.
Gilchrest et al., Plast. Reconstr. Surg. 1982; 69:278-83.
Welch et al., Neodymium-YAG Laser in Medicine, Stephen N. Joffe editor, 1983.

What is claimed is:

1. A method of treating skin of an individual, the method comprising:
    contacting the skin of the individual with a shield at a distal end of an applicator;
    transmitting radiofrequency energy in the form of an alternating current through a straight proximal portion of a copper tube in the applicator to generate a high frequency alternating magnetic field with a coil in a distal portion of the copper tube, wherein the coil is housed within the shield of the applicator;
    applying the high frequency alternating magnetic field to the skin to produce preferential heating of a dermis layer of the skin through inductive coupling with the dermis layer to treat the skin; and cooling the skin with a coolant applied by the applicator.

2. The method of claim 1, wherein the preferential heating of the dermis layer causes an effect in the dermis layer that is selected from the group consisting of coagulation, cauterization, contraction, shrinkage, induction of wound response, production of collagen, and a combination thereof.

3. The method of claim 1, wherein the preferential heating of the dermis layer activates collagen repair and growth in the dermis layer.

4. The method of claim 1, wherein the preferential heating of the dermis layer causes coagulation in the dermis layer, resulting in a reduced appearance of wrinkles in an epidermis layer of the skin.

5. The method of claim 1, further comprising monitoring the application of the high frequency alternating magnetic field with the applicator to provide feedback regarding the treating of the skin.

6. The method of claim 5, wherein monitoring the application of the high frequency magnetic field comprises applying a form of detection selected from the group consisting of detection of heat in the skin, detection of eddy currents in the dermis layer, detection of change in the dermis layer using ultrasound, detection of changes in impedance in the skin, and a combination thereof.

7. The method of claim 1, further comprising limiting an amount of capacitive coupling between the coil and the skin, using a Faraday shield disposed in the applicator between the coil and the shield.

8. The method of claim 1, wherein the cooling of the skin comprises circulating a coolant through the copper tube to cool the shield of the applicator.

9. The method of claim 1, wherein the cooling of the skin comprises directly applying a coolant to the skin via a coolant nozzle on the applicator.

10. The method of claim 1, wherein the step of cooling the skin is performed at least one of before, during, or after applying the high frequency alternating magnetic field.

11. The method of claim 1, further comprising moving a first capacitor ring in the applicator to adjust a size of a space between the first capacitor ring and a second capacitor ring to alter an impedance match between the applicator and a radiofrequency generator attached to the applicator.

12. A method of treating skin of an individual by inducing a wound response in a dermis layer of the skin, the method comprising:

contacting the skin of the individual with a shield at a distal end of an applicator;

transmitting radiofrequency energy in the form of an alternating current through a straight proximal portion of a copper tube in the applicator to generate a high frequency alternating magnetic field with a coil in a distal portion of the copper tube, wherein the coil is housed within the shield of the applicator; and applying the high frequency alternating magnetic field to the skin to produce preferential heating of the dermis layer of the skin through inductive coupling with the dermis layer, wherein the high frequency alternating magnetic field causes movement of ions in the dermis layer, thus inducing the wound response.

13. The method of claim 12, wherein inducing the wound response comprises at least one of activating collagen repair, activating collagen growth, or promoting dermal thickening.

14. The method of claim 12, further comprising cooling the skin with a coolant applied by the applicator.

15. The method of claim 14, wherein the cooling of the skin comprises circulating a coolant through the copper tube to cool the shield of the applicator.

16. The method of claim 14, wherein the cooling of the skin comprises directly applying a coolant to the skin via a coolant nozzle on the applicator.

* * * * *